(12) United States Patent
Cabibihan et al.

(10) Patent No.: US 11,229,534 B2
(45) Date of Patent: Jan. 25, 2022

(54) MULTIFUNCTIONAL TOOLING APPARATUS WITH NON-ANTHROPOMORPHIC CONSTRUCTION

(71) Applicant: QATAR UNIVERSITY, Doha (QA)

(72) Inventors: John-John Cabibihan, Pearl (QA); Aya Gaballa, The Pearl (QA); Mohammed Mudassir, Doha Jadeeda (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 16/858,126

(22) Filed: Apr. 24, 2020

(65) Prior Publication Data

US 2021/0330480 A1 Oct. 28, 2021

(51) Int. Cl.
*A61F 2/58* (2006.01)
*A61F 2/68* (2006.01)
*A61F 2/78* (2006.01)
*A61F 2/50* (2006.01)

(52) U.S. Cl.
CPC .............. *A61F 2/588* (2013.01); *A61F 2/583* (2013.01); *A61F 2002/5096* (2013.01); *A61F 2002/6854* (2013.01); *A61F 2002/7818* (2013.01)

(58) Field of Classification Search
CPC ................. A61F 2002/6854; A61F 2002/7818
See application file for complete search history.

(56) References Cited

U.S. PATENT DOCUMENTS

| 2,333,009 | A | * | 10/1943 | Hosmer | A61F 2/54 623/62 |
| 3,090,049 | A | | 5/1963 | Lanteigne | |
| 3,490,078 | A | | 1/1970 | Perez | |
| 3,802,302 | A | | 4/1974 | Bengtson | |
| 4,357,717 | A | * | 11/1982 | Puhl | A61F 2/588 623/61 |
| 4,585,363 | A | * | 4/1986 | McGuire | A61F 5/00 401/48 |
| 4,661,113 | A | * | 4/1987 | Adkins | A61F 2/588 473/229 |
| 5,314,500 | A | * | 5/1994 | Weddendorf | A61F 2/582 623/57 |
| 5,464,444 | A | * | 11/1995 | Farquharson | A61F 2/588 623/61 |

(Continued)

FOREIGN PATENT DOCUMENTS

| CN | 201782847 U | | 4/2011 |
| CN | 104783936 A | | 7/2015 |
| GB | 2278281 | * | 11/1994 |

OTHER PUBLICATIONS

Ottobock, "Body-powered Upper Limb Prostheses", URL: https://www.ottobock-export.com/en/prosthetics/upper-limb/solution-overview/arm-prostheses-body-powered/.

*Primary Examiner* — Bruce E Snow
(74) *Attorney, Agent, or Firm* — Squire Patton Boggs (US) LLP

(57) ABSTRACT

A prosthesis may include a fitted stump cover. The prosthesis may also include a socket fitted over the stump cover. The prosthesis may further include a ball attached to the socket. In addition, the prosthesis may include a shuttle locking mechanism attached in part to the ball. Further, the prosthesis may include a tool attached to the prosthesis by the shuttle locking mechanism.

6 Claims, 9 Drawing Sheets

(56) References Cited

U.S. PATENT DOCUMENTS

| | | | | |
|---|---|---|---|---|
| 6,416,555 | B1* | 7/2002 | Dillenburg | A61F 2/588 |
| | | | | 623/65 |
| 9,028,560 | B2 | 5/2015 | Farquharson et al. | |
| 10,702,404 | B2* | 7/2020 | Alley | A61F 2/78 |
| 2011/0058893 | A1* | 3/2011 | Merlo | F16C 11/10 |
| | | | | 403/104 |
| 2013/0331951 | A1* | 12/2013 | Doddroe | A61F 2/7812 |
| | | | | 623/36 |
| 2016/0374833 | A1* | 12/2016 | Dechev | A61F 2/54 |
| | | | | 623/62 |
| 2017/0266021 | A1* | 9/2017 | Bernhardt | A61F 2/7843 |

* cited by examiner

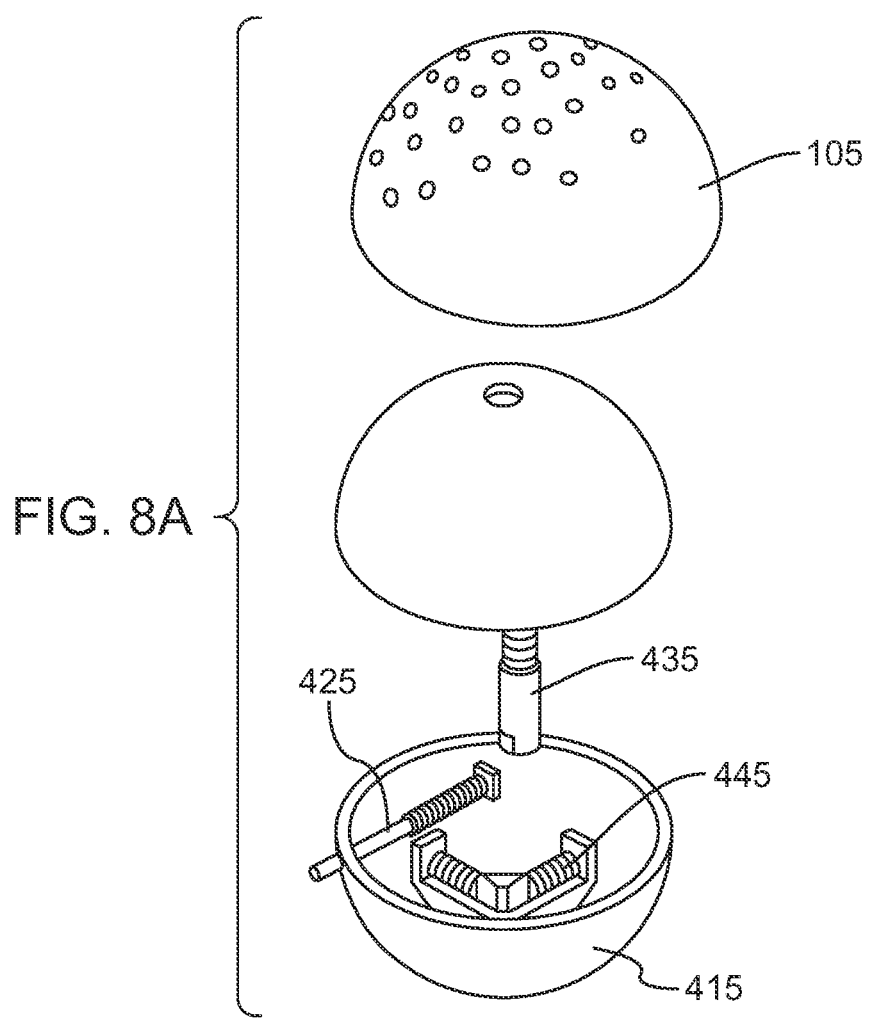

MULTIFUNCTIONAL TOOLING APPARATUS WITH NON-ANTHROPOMORPHIC CONSTRUCTION

FIELD OF INVENTION

Certain embodiments may generally relate to a limb prosthesis. More specifically, certain embodiments may generally relate to an upper-limb prosthesis, such as an artificial upper-limb prosthesis that may function as a tool-handling instrument.

BACKGROUND OF THE INVENTION

A prosthesis or artificial limb may often be used to replace a body part such as an arm, hand, or leg. With a prosthesis, a person can have the ability to perform daily activities independently and comfortably. That is, a prosthetic may enable a person to function and live as well or nearly as well as before. Prostheses may be created by hand or with computer-aided design (CAD), a software interface that helps creators design and analyze the creation with computer-generated 2-D and 3-D graphics, as well as analysis and optimization tools.

The majority of existing limb replacement solutions strive to restore limb functionality by attempting to recreate the shape and appearance of the natural limb. For example, existing limb replacement solutions strive to restore hand functionality by attempting to recreate the shape and appearance of a five-finger human hand. However, due to the complexities and dexterity present in a human hand or other limb, these mechanisms are often incredibly difficult to recreate, and devices often fall short due to their many limitations. Thus, there is a need to address these limitations by providing a device or prosthesis that circumvents these issues, and have the ability to act as a tool-handling instrument that does not require any grasping ability.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

SUMMARY OF THE INVENTION

Certain embodiments may be directed to a prosthesis. The prosthesis may include a fitted stump cover. The prosthesis may also include a socket fitted over the stump cover. In addition, the prosthesis may include a ball attached to the socket. The prosthesis may further include a shuttle locking mechanism attached in part to the ball. Furthermore, the prosthesis may include a tool attached to the prosthesis by the shuttle locking mechanism.

Other embodiments may be directed to a method. The method may include fitting a stump cover over a stump. The method may also include fitting a socket over the stump cover. The method may further include attaching a ball to the socket. In addition, the method may include attaching a shuttle locking mechanism to the ball. Further, the method may include attaching a tool to the ball by way of the shuttle locking mechanism.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 8(a) illustrates a main assembly, according to an embodiment.

Figure 1:
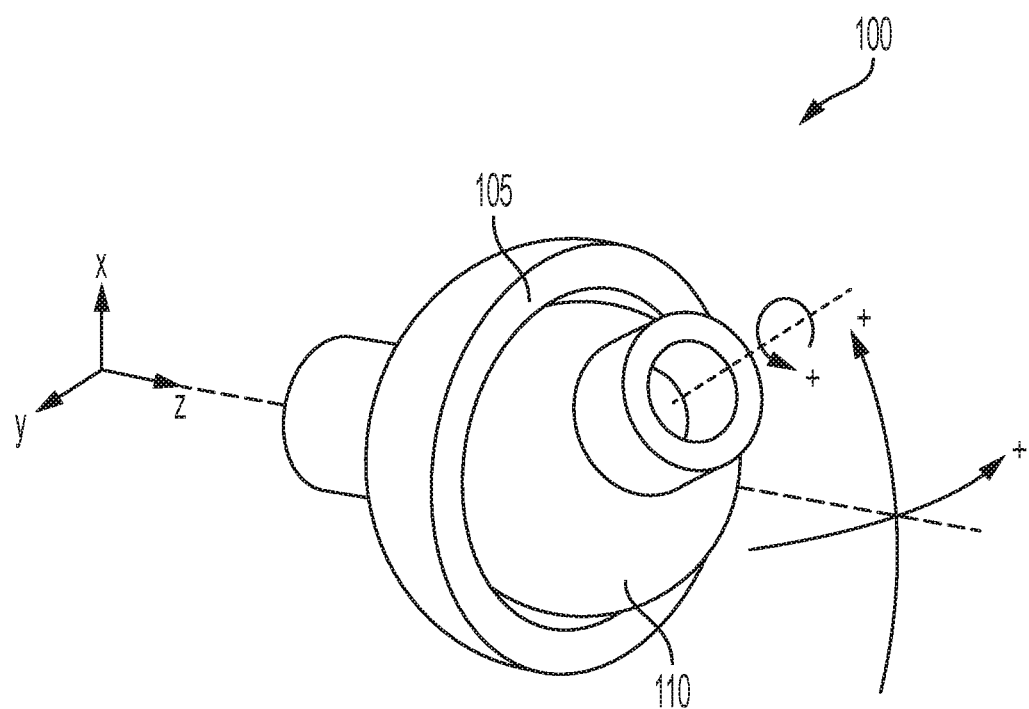
FIG. 1 illustrates a ball joint and socket system of a prosthesis, according to an embodiment.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. The following detailed description is, therefore, not to be taken in a limiting sense.

DETAILED DESCRIPTION

The features, structures, or characteristics of the invention described throughout this specification may be combined in any suitable manner in one or more embodiments. For example, the usage of the phrases "certain embodiments," "some embodiments," or other similar language, throughout this specification refers to the fact that a particular feature, structure, or characteristic described in connection with the embodiment may be included in at least one embodiment of the present invention.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical or structural changes may be made to the invention without departing from the spirit or scope of this disclosure. To avoid detail not necessary to enable those skilled in the art to practice the embodiments described herein, the description may omit certain information known to those skilled in the art. In addition, the examples described herein are for illustrative purposes only. The following detailed description is, therefore, not to be taken in a limiting sense.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

Certain embodiments may provide an artificial prosthesis, such as, for example, an upper-limb prosthesis. In other embodiments, the artificial prosthesis may be applied to a lower-limb as a lower-limb prosthesis. According to an embodiment, the prosthesis may have the ability to maximize functionality while maintaining minimal attention to replicating the appearance of a human limb (e g, hand, arm, leg, feet, etc.). For instance, in one embodiment, the prosthesis may act as a tool-handling instrument that does not require any grasping ability. Instead, the prosthesis may have the capability of having various tools attached thereto depending on certain uses of the prosthesis by the user of the prosthesis. According to certain embodiments, the prosthesis may be compatible with various tools including, for example, screwdrivers, wrenches, bar code scanners, paint brushes or paint rollers, nail pullers, and other tools. In addition, according to other embodiments, the prosthesis may be modular, and be modified to accommodate other tools and/or items including, for example, cooking utensils or toothbrushes. These additional items may be attached to the prosthesis to provide certain optimization capabilities based on the user's requirements.

Figure 6A:
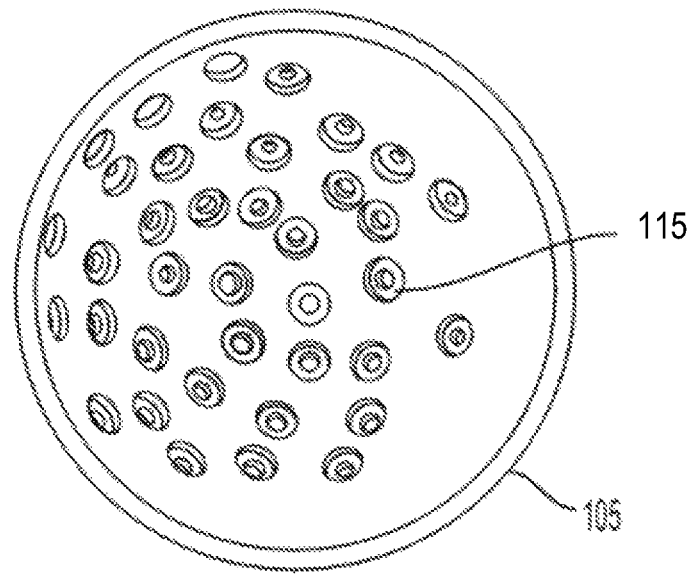
FIG. 6(a) illustrates an interior of a socket, according to an embodiment.
Figure 6B:
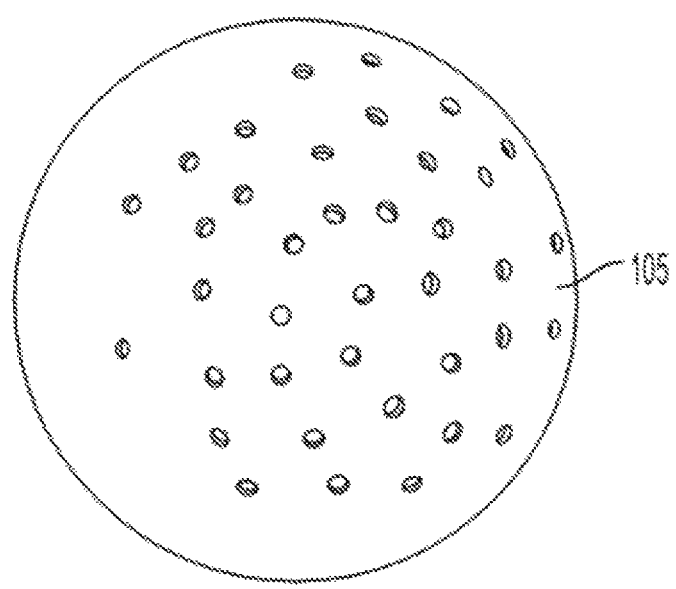
FIG. 6(b) illustrates an exterior of the socket, according to an embodiment.

FIG. 1 illustrates a ball joint and socket system of a prosthesis according to an embodiment. For instance, FIG. 1 illustrates a ball locking mechanism that may be used in place of the elbow and wrist joints. As illustrated in FIGS. 1, 6A and 6B, the ball joint and socket system 100 may include a socket 105 and a ball 110. In an embodiment, the ball 110 may be connected or attached to the socket 105. In certain embodiments, the socket 105 may be fitted over a stump of a person and strapped in place, either to the arm or over the shoulder, depending on the location of the stump. Furthermore, the socket 105 may take the shape of the stump for increased comfort and fitment. Beyond the stump, the prosthesis may take the limb's natural shape, such as the natural shape of an arm. According to an embodiment, for an arm prosthesis, if the stump is located above the elbow, the prosthesis may be fitted with a simple mechanical elbow joint that can take on the elbow's natural bent shape. Further, the elbow joint may also be adjusted to lock in other orientations to facilitate tool operation and increase device utility.

According to an embodiment, the elbow joint may include the ball and socket system 100 illustrated in FIG. 1. The ball and socket system 100 may provide a high range of motion without limiting degrees of freedom. To maintain sturdiness and stability during use, the ball 110 may be locked in place, thereby limiting all degrees of motion. In an embodiment, locking may be implemented in a number of ways. For example, in certain embodiments, locking may be implemented by tightening a thread over the ball 110 to prevent motion, or using a screw to hold the ball 110 in place. However, other embodiments may provide a locking mechanism that incorporates a series of retracting extrusions, or buttons, which may exist on the outer surface of the ball 110, and that can lock into corresponding slots in the socket's 105 inner surface. In such embodiments, to release the ball 110 and allow free rotation, a lever 405 (FIG. 4) may be attached to the side of the joint. When pulled, the lever may release the buttons to disengage locking. When the lever is engaged, the extrusions may be locked into corresponding slots on the inner surface of the ball socket 105. Further, when the lever is released, the extrusions may be retracted, and the mechanism may become unlocked, allowing for free rotation.

Figure 2C:
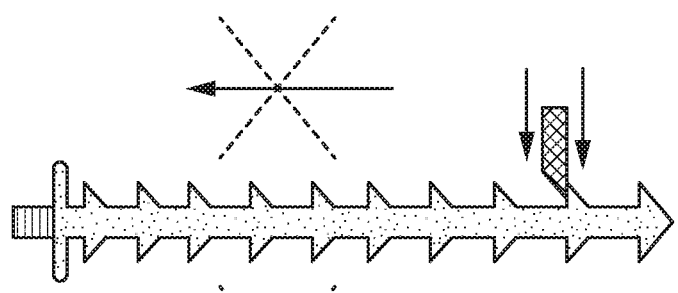
FIG. 2(c) illustrates a further operation of the shuttle lock mechanism, according to an embodiment.
Figure 2B:
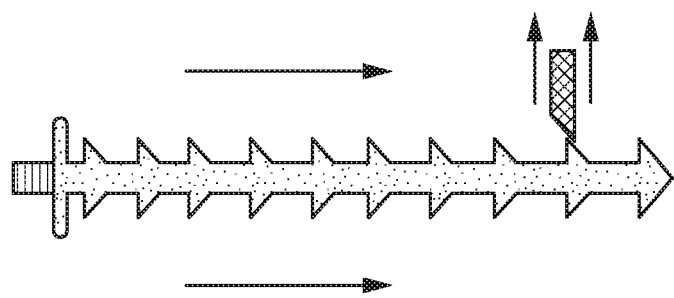
FIG. 2(b) illustrates another operation of the shuttle lock mechanism, according to an embodiment.
Figure 2A:
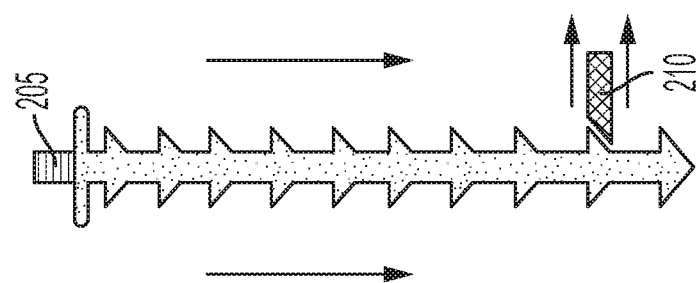
FIG. 2(a) illustrates an operation of a shuttle lock mechanism, according to an embodiment.

FIGS. 2(a)-2(b) illustrate a shuttle lock mechanism according to an embodiment. The shuttle lock mechanism illustrated in FIGS. 2(a)-2(b) is separate from the ball joint mechanism illustrated in FIG. 1. According to certain embodiments, the ball joint mechanism may be used for free wrist rotation, while the shuttle lock mechanism may be used for tool attachment in place of anthropomorphic hand grasping mechanics. In particular, FIG. 2(a) illustrates a shuttle lock mechanism in which a ribbed rod portion 205 is pushed past a holder 210 to lock the wrist connector of the prosthesis. FIG. 2(b) illustrates the shuttle lock mechanism in which the holder 210 is pulled back or released, thereby allowing the ribbed rod portion 205 to move in an upward or downward direction. Further, FIG. 2(c) illustrates the shuttle lock mechanism in which the holder 210 is engaged with the ribbed rod portion 205, preventing the ribbed rod portion 205 from moving backwards.

According to one embodiment, for a prosthesis of an arm, another ball locking mechanism may be provided at the wrist joint to maximize utility and increase device functionality. In particular, past the wrist joint, the prosthesis may include a shuttle lock mechanism such as that illustrated in FIGS. 2(a)-2(b). The shuttle lock mechanism may allow the prosthesis to be attached to specified tools or items. In an embodiment, the shuttle lock mechanism may include a ribbed rod portion 205 that may be pushed past a holder 210, preventing backwards motions and allowing the wrist connector with the lockable ball joint to stay in place (FIG. 2(a)). As illustrated in FIG. 2(b) the tool attached to the prosthesis may be removed or replaced by releasing the holder 210.

In certain embodiments, any compatible modification may be attached by inserting the ribbon rod portion 205 of the shuttle lock mechanism into the tool socket, and pushing it until an audible click is heard. By clicking the tool into place, stability may be ensured, and the user may be able to employ the attached part for the desired purpose. For example, in one embodiment, to screw a nail in place, the user may attach an appropriately sized screw onto the prosthesis, adjust the angles of the elbow and wrist joints, and control the rhythmic turning motion using their stump by rotating about the elbow or shoulder joint.

Figure 3C:
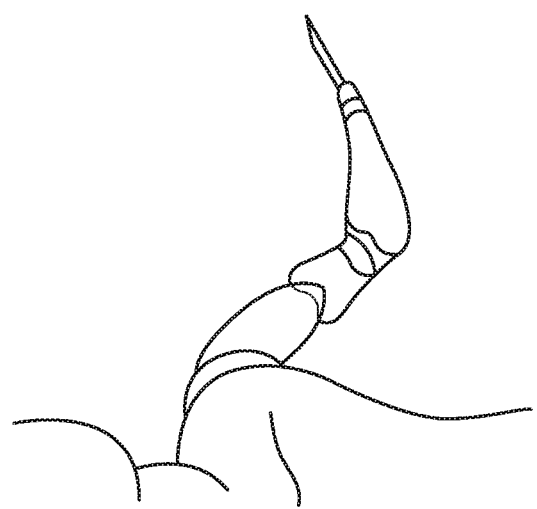
FIG. 3(c) illustrates the prosthesis with a screwdriver attached thereto, according to an embodiment.
Figure 3B:
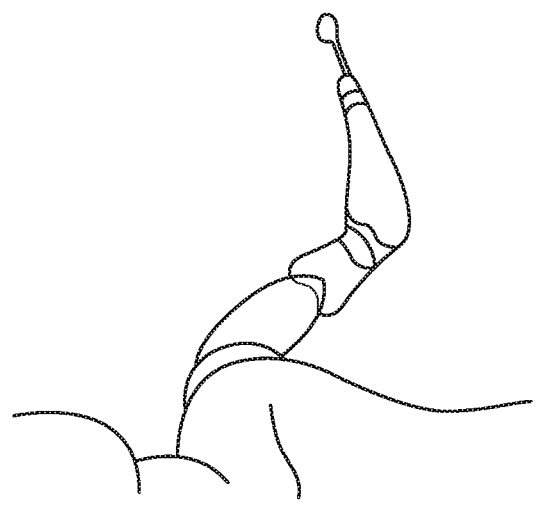
FIG. 3(b) illustrates the prosthesis with a spoon attached thereto, according to an embodiment.
Figure 3A:
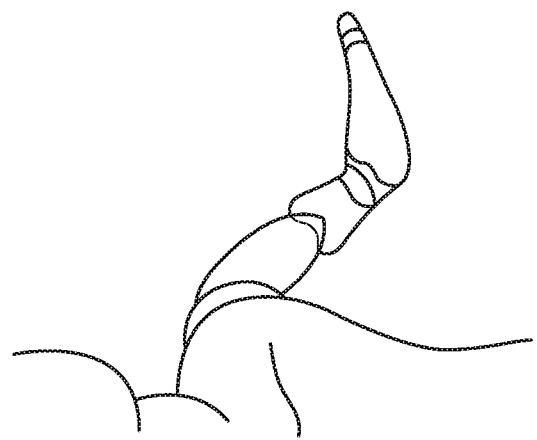
FIG. 3(a) illustrates the prosthesis with no tools attached, according to an embodiment.

FIG. 3(a) illustrates the upper-limb prosthesis with no tools attached according to an embodiment. FIG. 3(b) illustrates the upper-limb prosthesis with a spoon attached thereto according to an embodiment. Further, FIG. 3(c) illustrates the upper-limb prosthesis with a screwdriver attached thereto according to an embodiment. As illustrated in FIGS. 3(a)-3(c), it may be possible to use the upper-limb prosthesis in conjunction with various tools for added functionality. For example, as illustrated in FIGS. 3(a)-3(c), an extension piece capable of elongating and retracting into itself may be locked onto the wrist in conjunction with another tool. According to an embodiment, the tool may be a wrench using the same shuttle lock mechanism. As such, it may be possible to have an easy-to-use modifiable toolkit for individuals suffering from upper-limb loss.

FIGS. 3(a)-3(c) also illustrate the shuttle lock mechanism that is connected with the wrist ball joint, and may be used for tool attachment. In one embodiment, the ball mechanism may allow for free movement and adjustable device orientation until locked, whereas the shuttle lock may be used for stable object hold. According to certain embodiments, the shuttle lock mechanism may be used to eliminate the need for grasping by providing a simple but practical solution for tool fitting.

Figure 4:
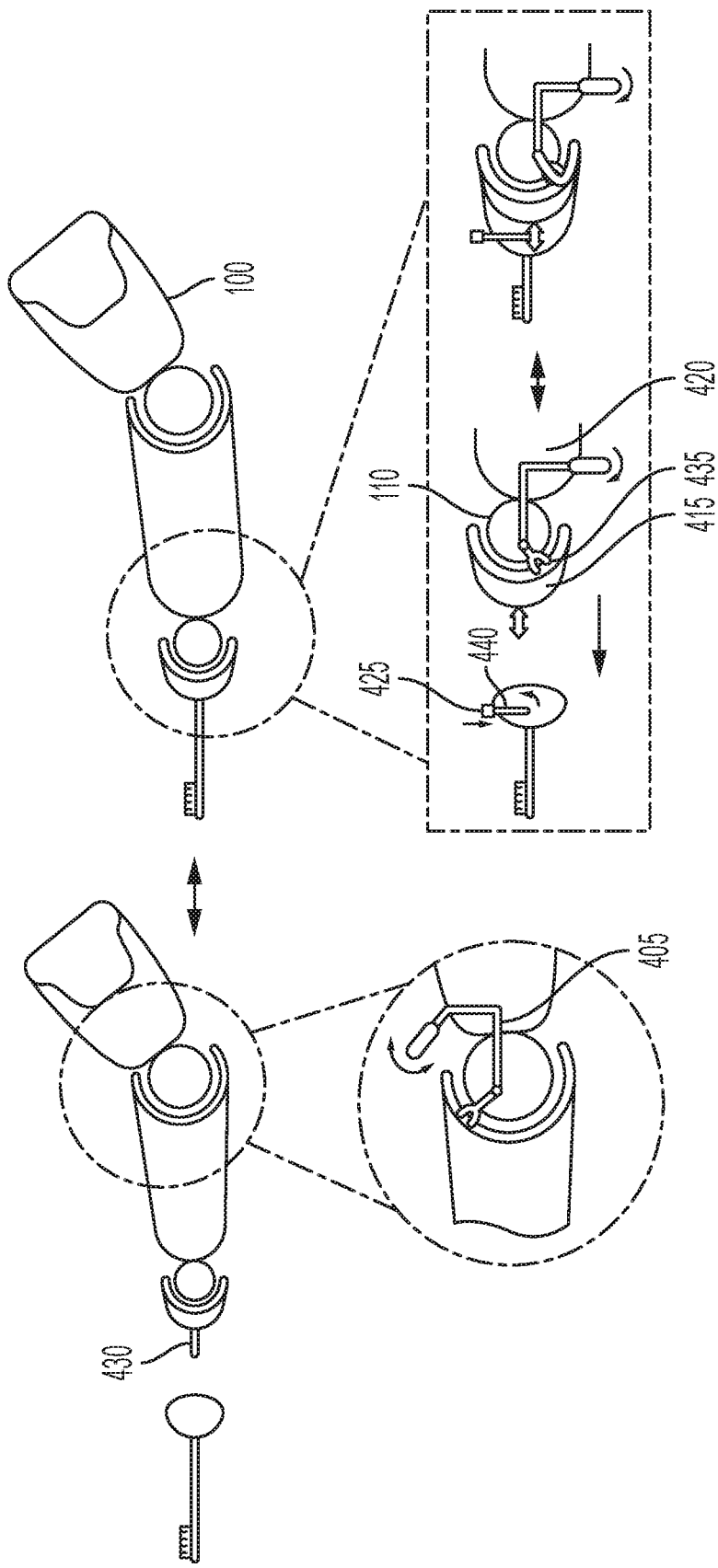
FIG. 4 illustrates a schematic of a prosthesis including cross-sectional views of various locking mechanisms, according to an embodiment.
Figure 7A:
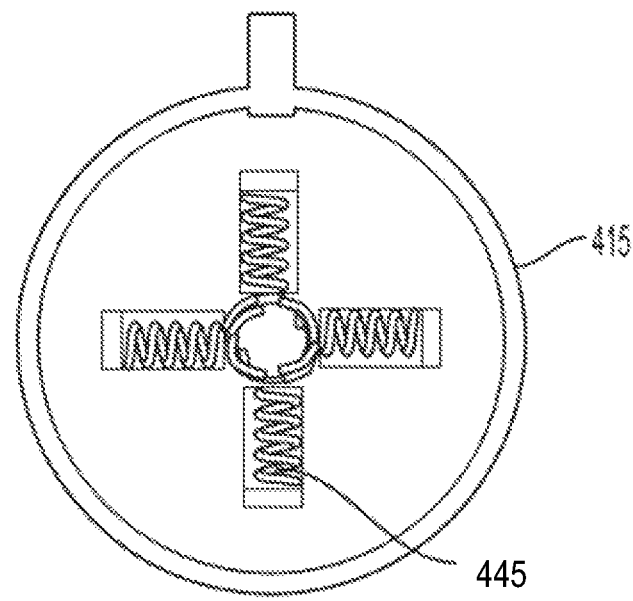
FIG. 7(a) illustrates a spring mechanism, according to an embodiment.
Figure 7B:
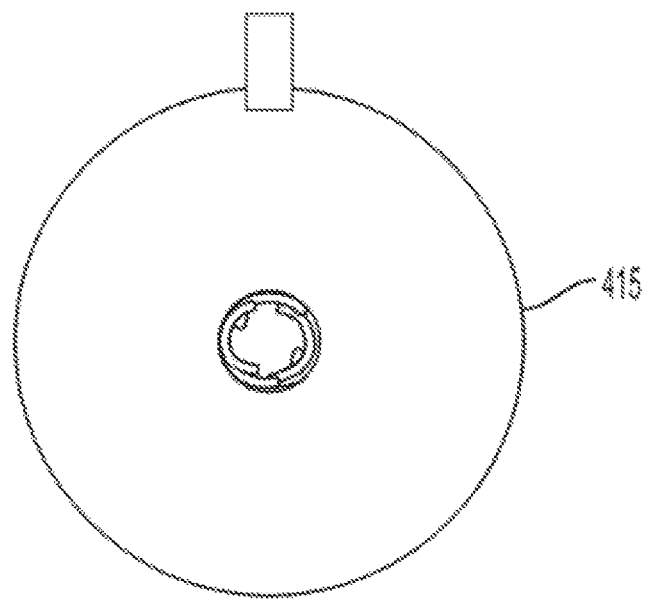
FIG. 7(b) illustrates an outer socket, according to an embodiment.
Figure 8B:
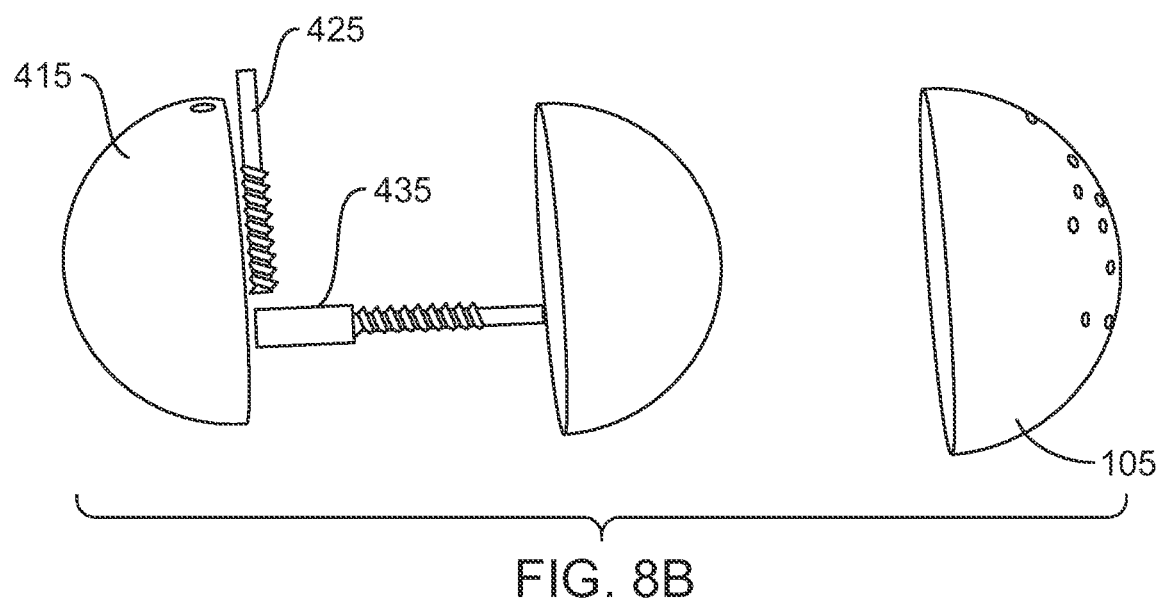
FIG. 8(b) illustrates a side view of the main assembly, according to an embodiment.

FIG. 4 illustrates a schematic of a prosthesis including cross-sectional views of various locking mechanisms according to an example embodiment. In particular, FIG. 4 illustrates a schematic of a prosthesis with locking mechanisms for the wrist joint and the elbow joint of the prosthesis, and how a tool may be attached to the prosthesis. FIG. 4 also illustrates a detailed view of the lever 405. According to an embodiment, the lever 405 may serve as a release mechanism, and may be applicable where extrusions are used to lock the ball joint. For instance, as illustrated in FIG. 4, the lever 405 (accessible to the user), may be attached to retractable extrusions on the ball's surface 110. According to certain embodiments, the attachment of the lever on the ball's surface 110 may use elbow joints or other joints on the body including, but not limited to, for example, the wrist joint. Further, as illustrated in FIGS. 4, 7(a), and 7(b), an outer socket 415 (see FIGS. 7A, 7B, 8A, and 8B) of the ball-socket mechanism may be attached to the ball's surface 110. In certain example embodiments, the outer socket 415 of the ball-socket mechanism may hold the ribbed rod portion 430 of the shuttle lock mechanism. In addition, FIG. 4 illustrates that the lever may be attached to the ball's surface 110 and a forearm portion 420 of the prosthesis.

Additionally, FIG. 4 illustrates a tool attachment process, with a focus on each of the ball joint mechanism and the shuttle lock mechanism. The bottom left plane illustrates a close-up of the ball joint mechanism, which may be applied at the elbow and the wrist to allow free joint rotation and adjustment. In an embodiment, the ball joint mechanism may also be shown without the locking lever 405, as illustrated in FIG. 1. Here, however, the lever 405 may be added to demonstrate the locking system. For instance, in FIG. 4, the arrow above the lever 405 symbolizes the movement necessary to lock and release the ball joint mechanism. In an embodiment, the lever 405 may be attached to extrusions on the surface of the ball 110 using an elbow connector and two springs. According to another embodiment, the extrusions may lock into corresponding holes 115 (see FIGS. 6A and 6B) on the inner surface of the ball socket 105. When the lever 405 is pulled, the balls may retract, causing the ball joint mechanism to be released, and the joint can freely rotate.

In an embodiment, the wrist portion of the device may have the exact same ball joint mechanism as the elbow joint mechanism, described above and displayed in the bottom left pane of FIG. 4, with one exception. Specifically, in the wrist portion of one embodiment, the outer socket of the ball joint mechanism 100 may also include a shuttle locking mechanism in place of the hand for tool attachment. In the top left pane of FIG. 4, the tool (in this case, a toothbrush), is unattached. However, on the top right side, the toothbrush may be attached using the shuttle lock mechanism (also illustrated in FIG. 3).

According to certain embodiments, the bottom right pane of FIG. 4 illustrates both mechanisms in the entire wrist joint. In particular, the ball joint mechanism, similarly to the elbow joint, may include a lever 405 connected to two extrusions 435 on the ball surface. In addition, the socket's outer surface may include the shuttle lock mechanism used to attach the tool (e.g., toothbrush). For instance, the tool in this case may include a push button that allows the shuttle lock mechanism to be released and the tool to be detached. The shuttle lock mechanism is also illustrated in detail in FIG. 3.

In certain embodiments, the shuttle lock mechanism may include a pin 440 on the inner surface of the attachable tool that is connected to a push button 425 on the outer surface. The arrow of where the pin 440 is located indicates the pin 440 movement as the push button 425 is pressed, and the arrow on the left side of the push button 425 indicates a pressing motion of the push button 425. If the button 425 is pressed, the pin 440 may mechanically bend out of the way, and the system may become disengaged, allowing the tool to be released. In another embodiment, if the button 425 is not pressed, the tool may be attached as shown in FIG. 4, by pushing it onto the shuttle mechanism until an audible click is heard. The mechanism then locks, and the tool is fixed in place until the button 425 is pushed to release the tool.

Certain embodiments described herein provide several technical improvements, enhancements, and/or advantages. In some embodiments, it may be possible to provide individuals suffering from limb loss with increased ability to perform simple tasks without the need for external help, and without the need to overexert to ensure adequate object grasping. As a result, this may allow them to gain the independence that they may lack with currently available artificial limb replacement devices. Certain embodiments may also provide a quick solution that provides the needed utility while requiring little to no training. Since there are no electrical or complex mechanical components, the device may also be low-cost to manufacture and sell, which makes it an ideal solution for underserved and war-torn communities.

According to other embodiments, it may be possible to assist those living with upper-limb loss, and benefit from basic tool handling either at home or at work. For instance, an attachable pencil or paintbrush may increase the user's ability for self-expression as well as increasing their likelihood to find suitable work. Utilities may also be extended to cooking and eating by attaching utensils such as spatulas, spoons, and kitchen knives. As more modifications are added, the device utility may be expanded to include increasing functionality.

Additionally, in other embodiments, by moving away from a human-hand lookalike, the device may take on a more industrial look, and avoid the possibility of a negative user response due to unwanted hand similarity. Certain embodiments may also enable the user to maximize the motion of the stump for device control. In addition, the user may be able to make the most use of the tools by shifting the axis of rotation from the wrist to the elbow or shoulders instead. Furthermore, since the device may be manually adjusted and not body-powered, it requires virtually no training to use and can be manufactured at low cost, thereby increasing reach and usability.

Figure 5:
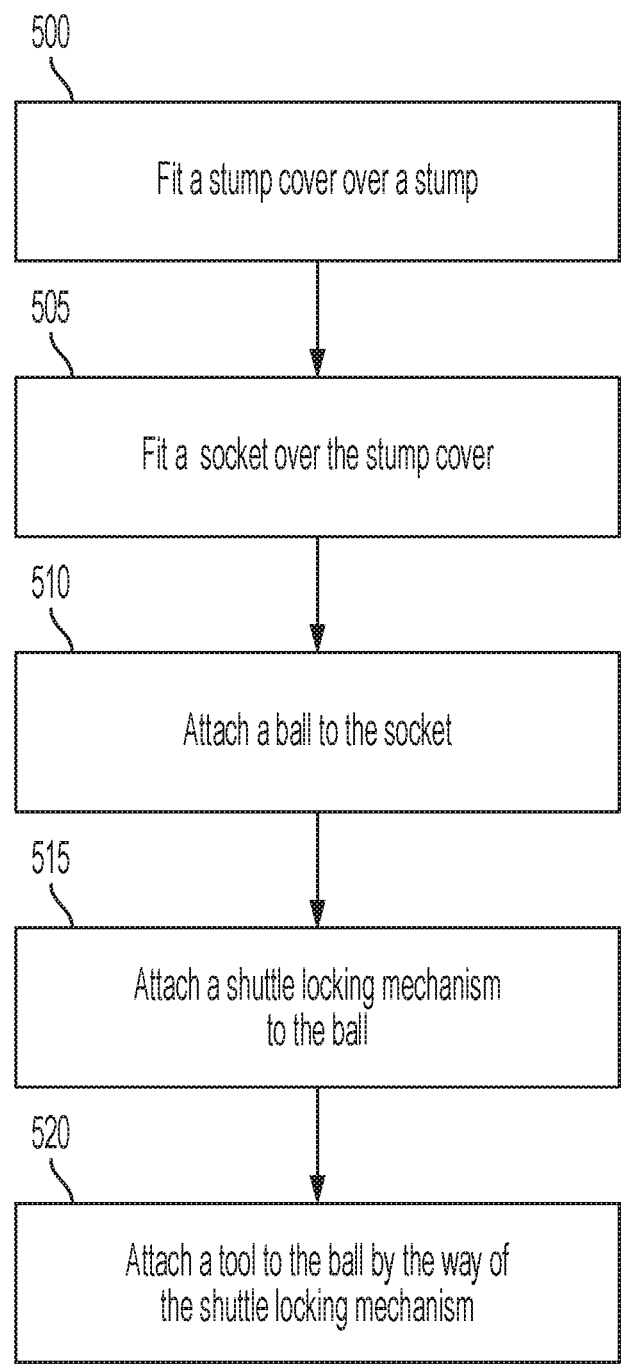
FIG. 5 illustrates a flow diagram of a method, according to an embodiment.

FIG. 5 illustrates a flow diagram of a method, according to an embodiment. According to an embodiment, the method of FIG. 5 may include, at 500, fitting a stump cover over a stump. The method may also include, at 505, fitting a socket over the stump cover. At 510, the method may include attaching a ball to the socket. Further, at 515, the method may include attaching a shuttle locking mechanism to the ball. At 520, the method may include attaching a tool to the ball by way of the shuttle locking mechanism.

In an embodiment, the shuttle locking mechanism includes a lever, a ribbed rod, and a holder. In another embodiment, the tool may be attached by pushing the ribbed rod past the holder until an audible click is heard. According to an embodiment, the ball may include a ball surface, and an extrusion on the ball surface. According to another embodiment, the shuttle locking mechanism may be connected to the extrusion on the ball surface. In further embodiments, the tool may include a push button, and the shuttle locking mechanism may include a pin connected to the push button, the pin located on an inner surface of the tool. In an embodiment, the pin may be configured to mechanically engage or disengage with the tool. In another embodiment, the shuttle locking mechanism may be connected to the extrusion 435 on the ball surface via a joint connector and one or more springs 445 (see FIGS. 7A and 8A). In a further embodiment, the extrusion may be locked into corresponding holes on an inner surface of the socket, and the tool may be attached and detached by engaging the lever.

One having ordinary skill in the art will readily understand that the invention as discussed above may be practiced with steps in a different order, and/or with hardware elements in configurations which are different than those which are disclosed. Therefore, although the invention has been described based upon these example embodiments, it would be apparent to those of skill in the art that certain modifications, variations, and alternative constructions would be apparent, while remaining within the spirit and scope of example embodiments.

We claim:

1. A ball and socket system, comprising:
a ball;
a socket fitted over the ball, wherein the socket comprises a ribbed rod portion protruding from an exterior surface of the socket;
a tool comprising a base portion, wherein the tool is attached to the exterior surface of the socket at the base portion via the ribbed rod portion; and
a pin connected to a first push button, wherein the pin is configured to lock the tool to the socket by operating the first push button to mechanically engage the pin with the ribbed rod portion.

2. The ball and socket system according to claim 1,
wherein the socket comprises a plurality of holes, and
wherein the ball defines a top hole configured to be aligned with one of the plurality of holes of the socket, and
wherein the ball comprises a locking mechanism housed in an interior space of the ball.

3. The ball and socket system according to claim 2, wherein the locking mechanism comprises:
an extrusion extending through the top hole of the ball and one of the plurality of holes of the ball; and
a second push button configured to lock the extrusion and maintain a connection between the socket and the ball.

4. A method, comprising:
attaching a socket to an outer surface of a ball, wherein the socket comprises a ribbed rod portion protruding from an exterior surface of the socket;
attaching a tool to the exterior surface of the socket at a base portion of the tool via the ribbed rod portion;
locking the tool to the socket via a pin connected to a first push button; and
operating the first push button to lock the tool to the socket by mechanically engaging the pin with the ribbed rod portion.

5. The method according to claim 4,
wherein the socket comprises a plurality of holes, and the ball defines a top hole, and
wherein the method further comprises aligning the top hole of the ball with one of the plurality of holes of the socket.

6. The method according to claim 5,
wherein the socket is attached to the outer surface of the ball via a locking mechanism,
wherein the locking mechanism comprises
an extrusion extending through the top hole of the ball and one of the plurality of holes of the socket, and
a second push button configured to lock the extrusion and maintain a connection between the socket and the ball.

* * * * *